US00PP28835P3

(12) United States Plant Patent
Waterworth

(10) Patent No.: US PP28,835 P3
(45) Date of Patent: Jan. 2, 2018

(54) ***METROSIDEROS* PLANT NAMED 'METWAT01'**

(50) Latin Name: *Metrosideros collina*
Varietal Denomination: METWAT01

(71) Applicant: Josh Waterworth, Glass House Mountains (AU)

(72) Inventor: Josh Waterworth, Glass House Mountains (AU)

( * ) Notice: Subject to any disclaimer, the term of this patent is extended or adjusted under 35 U.S.C. 154(b) by 0 days.

(21) Appl. No.: 14/999,566

(22) Filed: May 26, 2016

(65) Prior Publication Data

US 2017/0347513 P1 Nov. 30, 2017

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Cassandra Bright

(57) ABSTRACT

A new and distinct *Metrosideros collina* named 'METWAT01' is disclosed, characterized by variegated foliage and bright red new growth. The new cultivar is a *Metrosideros collina*, typically suited for ornamental landscape use.

2 Drawing Sheets

Latin name of the genus and species: *Metrosideros collina.*

Variety denomination: 'METWAT01'.

BACKGROUND OF THE INVENTION

The new cultivar is the result of chance discovery in a commercial nursery in Queensland, Australia. The inventor, Josh Waterworth, discovered the new variety as a single branch, naturally occurring mutation growing in a commercial planting of the parent variety *Metrosideros collina*, unpatented. The discovery was made in March of 2010.

First propagation was performed by terminal semi-softwood vegetative cuttings during March of 2008. This occurred at the nursery of discovery, in Queensland, Australia. The inventor continued confidential testing and evaluation of the new variety at this location. After propagation of 5 generations, the inventor made a final selection of the variety for commercial purposes, determining the mutation to be stable and re-produceable. Since the initial selection in 2008, 6 generations have been propagated.

SUMMARY OF THE INVENTION

The cultivar 'METWAT01' has hot been observed under all possible environmental conditions. The phenotype may vary somewhat with variations in environment such as temperature, day length, and light intensity, without, however, any variance in genotype.

The following traits have been repeatedly observed and are determined to be the unique characteristics of 'METWAT01'. These characteristics in combination distinguish 'METWAT01' as a new and distinct *Metrosideros* cultivar:

1. Vibrant red new growth
2. Uniquely variegated foliage.
3. Suitability for hedging.

PARENTAL COMPARISON

Plants of the new cultivar 'METWAT01' are similar to the parent, in most horticultural characteristics. However, 'METWAT01' differs in foliage color. Mature foliage of the new variety is distinctly yellow with a green margin. Mature foliage of the parent variety is solid green

COMMERCIAL COMPARISON

Plants of the new cultivar 'METWAT01' can be compared to the patented commercial variety *Metrosideros* 'Tahitian Sunset' U.S. Plant Pat. No. 20,492. Plants of 'METWAT01' are similar to 'Tahitian Sunset' in most horticultural characteristics, however, 'METWAT01' differs in the following:

1. Mature plants of the new variety reach approximately 3 meters tall, mature plants of this comparator reach approximately 1 meter tall.
2. Foliage of the new variety is longer and wider.
3. Foliage of the new variety is slightly reflexed back, foliage of this comparator is somewhat twisted.

BRIEF DESCRIPTION OF THE PHOTOGRAPHS

Figure 1:
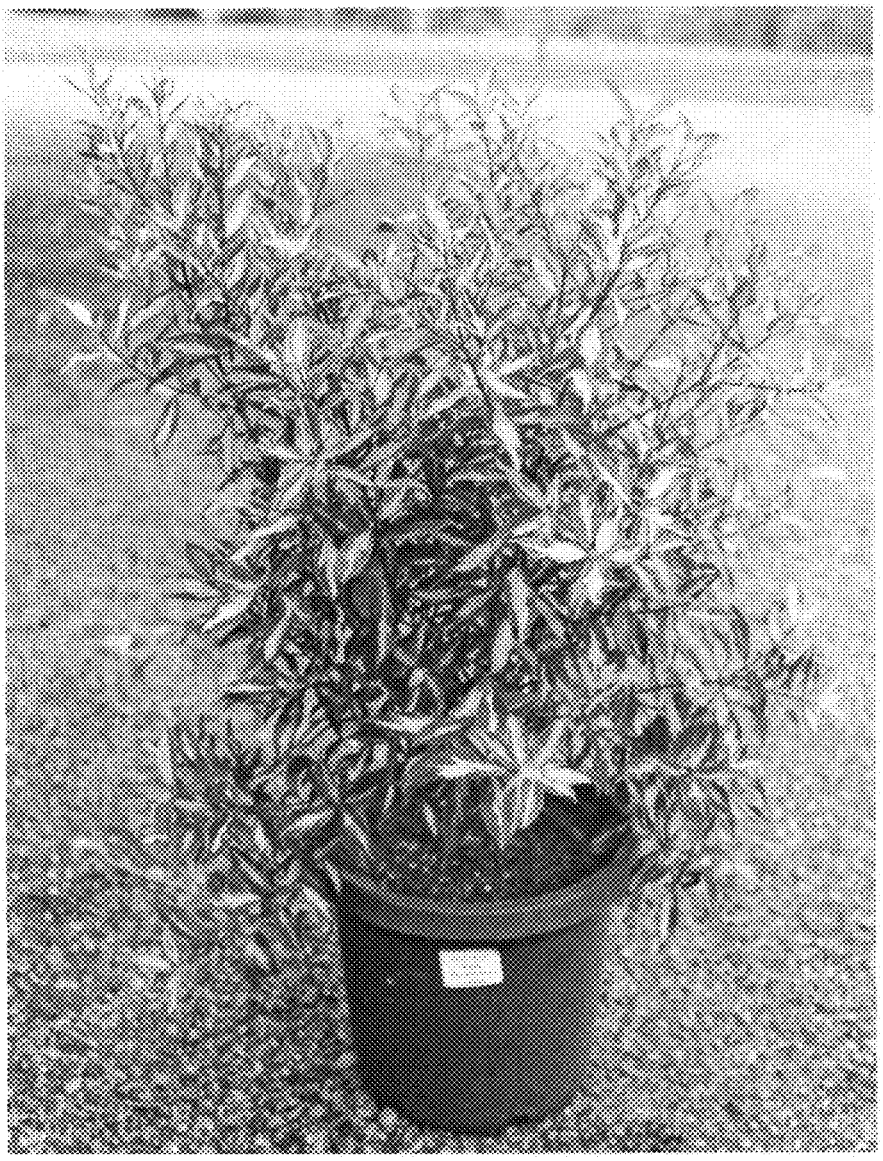

The accompanying photograph in FIG. 1 illustrates in full color a typical plant of 'METWAT01' grown outdoors in Silvan, Victoria, Australia This plant is approximately 20 months old, shown in a 10 liter pot.

Figure 2:
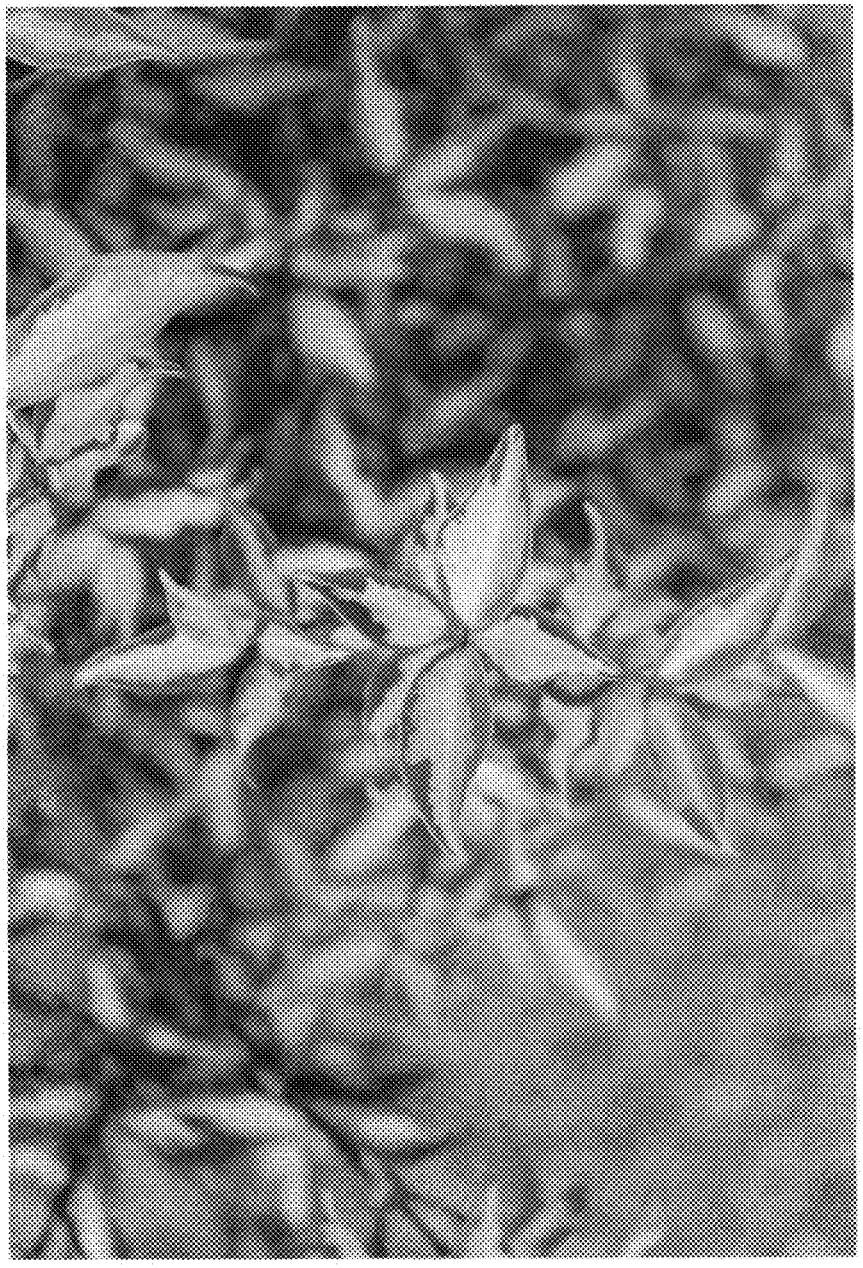

FIG. 2 illustrates a close up of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'METWAT01' plants grown outdoors in Silvan, Victoria, Australia. Temperatures ranged from approximately 7° C. to 10° C. at night to 15° C. to 30° C. during the day. No artificial light, photoperiodic treatments or chemical treatments were given to the plants. Measurements and numerical values represent averages of typical plant types.

GENERAL INFORMATION

Botanical classification: *Metrosideros collina* 'METWAT01'.
Age of the plant described: Approximately 3 years.
Container size of the plant described: Planted in the ground.

PROPAGATION

Time to initiate roots: Summer: 30 to 40 days at approximately 22° C.
Root description: Fine, densely branched, non-fibrous, non-fleshy. Brown and light brown, not accurately measured with The R.H.S. chart.

PLANT

Growth habit: Upright.
Height: Approximately 3 meters from soil line to top leaf, after 3 years.
Plant spread: Approximately 2 meters after 3 years.
Stem diameter: Approximately 0.2 cm.
Stem color: New growth new Red-Purple 59A, maturing to Brown 200C.
Stem texture: Glabrous.
Branching characteristics: Moderately well-branched, bushy and upright habit. Branches occurring at acute angles.
Length of primary lateral branches: Average range from 20 to 125 cm.

FOLIAGE

Leaf:
*Arrangement*.—Opposite, single
*Average leaves per lateral branch*.—Approximately 10 to 20. .
*Average length*.—4.5 to 6 cm.
*Average width*.—2.5 cm.
*Shape of blade*.—Lanceolate.
*Apex*.—Acute.
*Base*.—Rounded.
*Margin*.—Entire.
*Pubescence*.—Some pubescence upper and lower surfaces with maturity.
*Aspect*.—Somewhat reflexed back.
*Color*.—New young foliage upper side: Near RHS Red 46C. New young foliage under side: Near RHS Red 46C. Young foliage upper side: Largest part near Yellow-Orange 14D, flushed Orange-Red 45B, margin near Yellow-Green 152D. Young foliage under side: Largest part near Yellow-Orange 14D, flushed Orange-Red 45B, margin near Yellow-Green 152D. Mature foliage upper side: Center near RHS Yellow-Green 151C, margin near Green N137B. Mid-vein near Red-Purple 60A. Mature foliage under side: Center near RHS Yellow-Green 151C, margin near Green N137B. Mid-vein near Red-Purple 60A.
*Venation*.—Type: Pinnate. Venation color upper side: Prominent mid-vein near Red-Purple 60A. Lateral veins near Yellow-Green 151C. Venation color under side: Prominent mid-vein near Red-Purple 60A. Lateral veins near Yellow-Green 151C.

OTHER CHARACTERISTICS

Seeds and fruits: Not observed to date.
Disease/pest resistance: Good resistance to normal diseases and pests of *Metrosideros* has been observed.
Temperature tolerance: USDA zones 10 through 13.
Other tolerances: Very drought tolerant. Tolerant of sandy soil conditions.

What is claimed is:

1. A new and distinct cultivar of *Metrosideros collina* plant named 'METWAT01' as herein illustrated and described.

* * * * *